United States Patent
Nessel et al.

(10) Patent No.: US 10,682,459 B2
(45) Date of Patent: Jun. 16, 2020

(54) DRUG DELIVERY DEVICE WITH ELECTROMAGNETIC DRIVE UNIT

(71) Applicant: Sanofi-Aventis Deutschand GmbH, Frankfurt am Main (DE)

(72) Inventors: Christian Nessel, Frankfurt am Main (DE); René Richter, Tharandt (DE); Robert Witt, Dresden (DE); Richard Guenther, Dresden (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 254 days.

(21) Appl. No.: 15/538,729

(22) PCT Filed: Dec. 18, 2015

(86) PCT No.: PCT/EP2015/080674
§ 371 (c)(1),
(2) Date: Jun. 22, 2017

(87) PCT Pub. No.: WO2016/102407
PCT Pub. Date: Jun. 30, 2016

(65) Prior Publication Data
US 2017/0368256 A1 Dec. 28, 2017

(30) Foreign Application Priority Data
Dec. 22, 2014 (EP) .................................... 14199552

(51) Int. Cl.
*A61M 5/14* (2006.01)
*A61M 5/142* (2006.01)
(Continued)

(52) U.S. Cl.
CPC .......... *A61M 5/14212* (2013.01); *A61M 5/20* (2013.01); *A61M 5/30* (2013.01);
(Continued)

(58) Field of Classification Search
CPC ...... A61M 5/14212; A61M 5/24; A61M 5/30; A61M 5/20; H02P 8/34; H02P 25/066;
(Continued)

(56) References Cited

U.S. PATENT DOCUMENTS 2,550,053 A * 4/1951 Ferguson ................ A61M 5/30
604/68
4,965,864 A * 10/1990 Roth .................... H02K 41/031
310/12.19

(Continued)

FOREIGN PATENT DOCUMENTS

| CN | 102247637 | 11/2011 |
|---|---|---|
| DE | 10229689 | 1/2004 |

(Continued)

OTHER PUBLICATIONS

International Preliminary Report on Patentability in International Application No. PCT/EP2015/080674, dated Jun. 27, 2017, 7 pages.
International Search Report and Written Opinion in International Application No. PCT/EP2015/080674, dated Feb. 29, 2016, 11 pages.

*Primary Examiner* — Amber R Stiles
(74) *Attorney, Agent, or Firm* — Fish & Richardson P.C.

(57) ABSTRACT

The disclosure relates to a drug delivery device having a drive unit includes a stator comprising a plurality of coils consecutively arranged in an axial direction, and an armature axially movable within the stator, the armature including a number of magnets and pole shoes consecutively arranged in the axial direction. A respective pole shoe is arranged between respectively neighbouring magnets. At least one axial end of the armature comprises a terminal pole shoe.

15 Claims, 3 Drawing Sheets

(51) Int. Cl.
*H02K 41/03* (2006.01)
*H02P 8/00* (2006.01)
*A61M 5/30* (2006.01)
*H02K 11/225* (2016.01)
*A61M 5/20* (2006.01)
*H02P 25/066* (2016.01)
*H02P 8/34* (2006.01)
*A61M 5/24* (2006.01)

(52) U.S. Cl.
CPC ......... *H02K 11/225* (2016.01); *H02K 41/031* (2013.01); *H02P 8/005* (2013.01); *H02P 8/34* (2013.01); *H02P 25/066* (2016.02); *A61M 5/24* (2013.01); *H02P 2203/01* (2013.01)

(58) Field of Classification Search
CPC ...... H02P 8/005; H02P 2203/01; H02P 25/06; H02K 41/031; H02K 11/225
See application file for complete search history.

(56) References Cited

U.S. PATENT DOCUMENTS

2013/0025986 A1* 1/2013 Lee ................... H02K 41/031
    188/267
2014/0361641 A1 12/2014 Satou et al.

FOREIGN PATENT DOCUMENTS

| DE | 10229689 A1 * | 1/2004 | ............ H02K 41/03 |
|----|---------------|--------|------------------------|
| GB | 2358967 | 8/2001 | |
| JP | 2001-520498 | 10/2001 | |
| JP | 2014-007922 | 1/2014 | |
| WO | WO 99/09972 | 4/1999 | |
| WO | WO 2014/180804 | 11/2014 | |

* cited by examiner

DRUG DELIVERY DEVICE WITH ELECTROMAGNETIC DRIVE UNIT

CROSS-REFERENCE TO RELATED APPLICATIONS

This application is a U.S. national stage application under 35 USC § 371 of International Application No. PCT/EP2015/080674, filed on Dec. 18, 2015, which claims priority to European Patent Application No. 14199552.2, filed on Dec. 22, 2014, the entire contents of which are incorporated herein by reference.

TECHNICAL FIELD

The disclosure relates to a drive unit, in particular for a drug delivery device.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices, the energy to deliver the fluid is provided by a drive unit such as a spring or an electric motor.

There remains a need for an improved drive unit, in particular for a drug delivery device.

SUMMARY

The present disclosure provides an improved drive unit, in particular for a drug delivery device.

According to the disclosure, a drive unit comprises:
a stator comprising a plurality of coils consecutively arranged in an axial direction,
an armature axially movable within the stator, the armature comprising a number of magnets and pole shoes consecutively arranged in the axial direction, wherein a respective pole shoe is arranged between respectively neighbouring magnets, wherein at least one axial end of the armature comprises a terminal pole shoe.

The drive unit may thus be applied as a linear actuator in a drug delivery device, e.g. by applying an alternating voltage to the coils.

In an exemplary embodiment, the at least one terminal pole shoe differs from the pole shoes in its geometry, in particular in its axial length such that one of the coils, in which the terminal pole shoe is located has a different inductance than any one of the coils, in which one of the pole shoes is located.

In an exemplary embodiment, a control unit is connected to the individual coils for determining their inductance, wherein the control unit is adapted to determine an axial position of the armature within the stator from the determined inductances.

Thus allows for determining an axial position of the armature within the stator by determining the inductances of the coils and locating the one with an inductance differing from all the other inductances. The drive unit is thus used for both, driving the armature and determining its axial position such that no further sensor is required.

In an exemplary embodiment, the stator further comprises a plurality of notched metal sheets in an alternating arrangement with the coils.

In an exemplary embodiment, the magnets are axially magnetized.

In an exemplary embodiment, consecutive ones of the magnets exhibit alternating magnetic polarities.

In an exemplary embodiment, the drive unit is applied in a drug delivery device, further comprising a drug cartridge with a stopper slidably arranged within the cartridge, wherein the armature abuts the stopper. The drive unit can thus be used for displacing the stopper and dispensing a dose of drug from the cartridge. Furthermore, the drive unit can be used to determine the position of the armature and hence the stopper in order to determine an amount of drug already delivered and/or an amount of drug remaining in the cartridge.

In an exemplary embodiment, the coils of the stator are subdivided into a first group and a second group, the first group extending proximally from the cartridge along a distance corresponding to a length of the armature, wherein the second group is coaxially arranged over at least a substantial part of the length of the cartridge, wherein the second group of coils has an increased air gap between the notched metal sheets and the pole shoes compared to the first group in order to allow insertion of the cartridge.

In an exemplary embodiment, the air gap between the first group and the armature is less than 1 mm thus efficiently using the available space and achieving a high degree of efficiency. The magnetic latching forces and thrust forces acting on the armature are significantly determined by the air gap between the notched metal sheets and the pole shoes. This allows for a precise adaptation to the requested thrust parameters in the operating area of the first group.

In an exemplary embodiment, an inner diameter of notches varies such that a gradient of thrust forces or latching forces acting on the armature converges to a given characteristic line. In an exemplary embodiment the restriction line is linearly decaying.

In an exemplary embodiment, a relation between an external diameter of the stator and an external diameter of the cartridge is within a range from 1.5 to 3, in particular 2.2.

In an exemplary embodiment, a relation between an external diameter of the armature and an internal diameter of the stator is within a range from 0.8 to 0.99, in particular 0.95.

In an exemplary embodiment, a relation between a length of one of the poles shoes and a length of one of the terminal pole shoes is within a range from 0.3 to 0.5, in particular 0.43 and/or a magnetic permeability of one of the pole shoes differs from a magnetic permeability of one of the terminal pole shoes. Thus, the inductances of two adjacent coils may significantly differ as the terminal pole show passes such that the position of the armature can be more precisely determined.

In an exemplary embodiment, a relation between the air gap in the operating range of the first group of coils and an external diameter of the cartridge is within a range from 0.01 to 0.05, in particular 0.02.

Further scope of applicability of the present disclosure will become apparent from the detailed description given hereinafter. However, it should be understood that the detailed description and specific examples, while indicating exemplary embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The present disclosure will become more fully understood from the detailed description given hereinbelow and the accompanying drawings which are given by way of illustration only, and thus, are not limitive of the present disclosure, and wherein.

Corresponding parts are marked with the same reference symbols in all figures.

DETAILED DESCRIPTION

Figure 1:
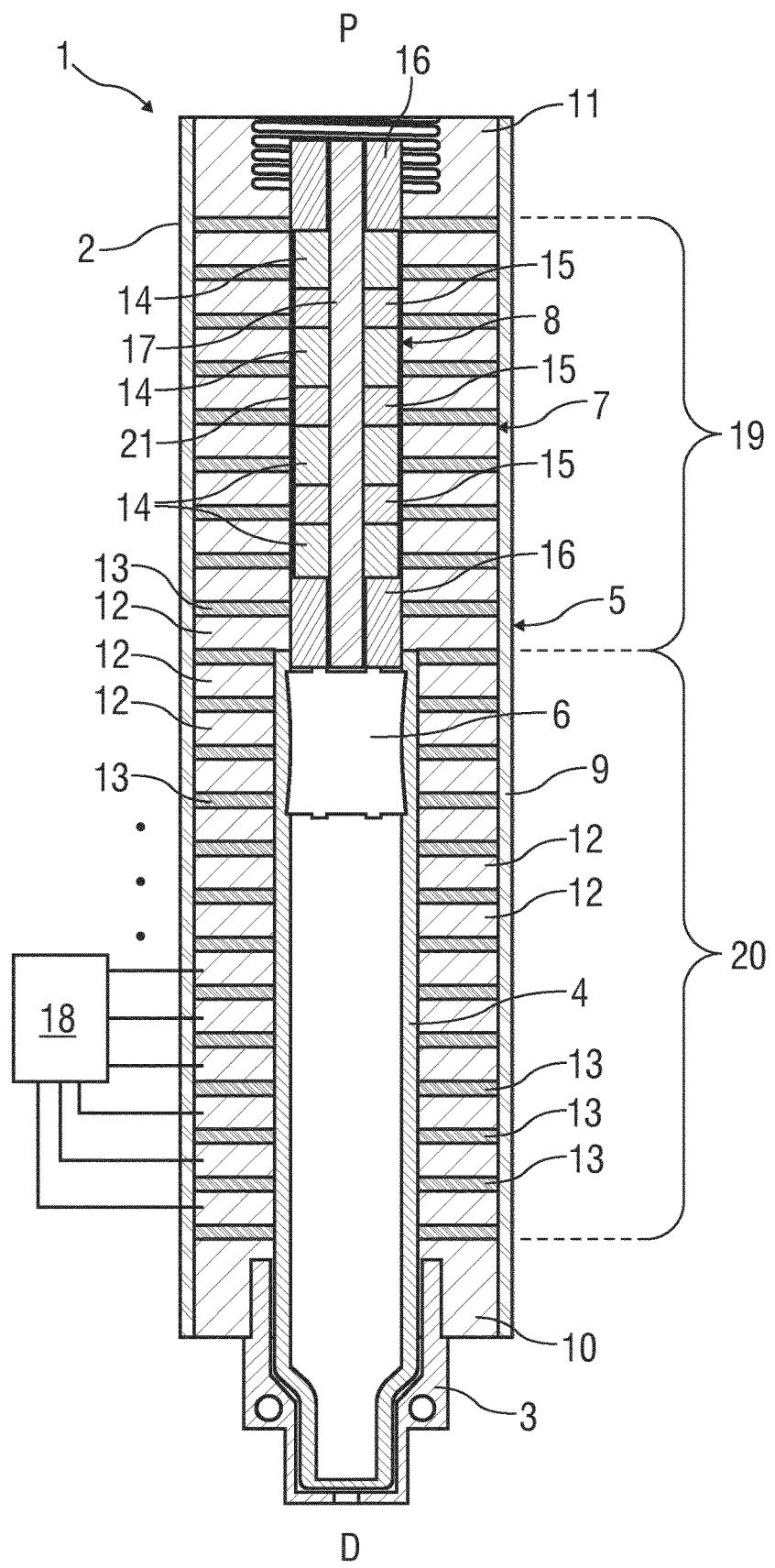
FIG. 1 is a schematic longitudinal section of an exemplary embodiment of a drug delivery device with a drive unit comprising an armature, a first group of coils and a second group of coils.

FIG. 1 is a schematic longitudinal section of an exemplary embodiment of a drug delivery device 1. The drug delivery device 1 comprises an elongate case 2, a cartridge holder 3, a drug cartridge 4 and a drive unit 5.

In an exemplary embodiment, the case 2 may have a tubular shape. The cartridge holder 3 may be axially and radially fixed to the case 2. The drug cartridge 4 may be arranged as an ampoule or syringe adapted to be connected to a nozzle such as a hypodermic needle or having an attached nozzle. In an exemplary embodiment, the cartridge 4 may comprise or consist of glass or a plastic material. A stopper 6 is slidably arranged within the cartridge 4 so as to seal the cartridge 4 proximally and allow displacement of a drug held within the cartridge 4 on translation of the stopper 6 in a distal direction D relative to the cartridge 4. The nozzle may also be arranged as a jet nozzle for needleless injection or as a spray nozzle. In an exemplary embodiment the cartridge 4 is replaceable.

The drive unit 5 comprises a stator 7 and an armature 8 axially movable within the stator 7 and arranged to abut the stopper 6. The stator 7 comprises a ferromagnetic tube 9 also serving as the case 2 in the illustrated embodiment. In an exemplary embodiment, the tube 9 may be axially split such that it comprises two axially aligned tube sections. Likewise, these internal components may be fixed to the tube 9 in a different way. The stator 7 furthermore comprises a number of coils 12, e.g. copper coils, and notched metal sheets 13 in an alternating arrangement such that a metal sheet 13 is axially followed by a coil 12, another metal sheet 13 and another coil 12 and so on. In an exemplary embodiment, the stator comprises 21 coils 12 and 22 notched metal sheets 13. The skilled person will understand that any other number of coils and notched metal sheets 13 may be arranged. However, in an exemplary embodiment, the number of notched metal sheets 13 exceeds the number of coils 12 by one.

The armature 8 comprises a number of axially magnetized magnets 14, e. g. rare earth magnets such as neodymium magnets comprising iron and neodymium. A number of these magnets 14 are consecutively arranged along an axial direction with alternating magnetic polarity. A respective pole shoe 15 comprising or consisting of a ferromagnetic material is arranged between neighbouring magnets 14 and a respective terminal pole shoe 16 comprising or consisting of a ferromagnetic material at each axial end of the sequence of magnets 14 and pole shoes 15. The pole shoes 15, terminal pole shoes 16 and the magnets 14 may have central bores allowing them to be arranged on a non-ferromagnetic axle 17 which may comprise or consist of a non-ferromagnetic stainless steel. A protective layer such as a heat shrink hose may be arranged over the armature 8 for mechanically protecting the armature 8.

In an exemplary embodiment, the armature 8 comprises four magnets 14, three pole shoes 15 and two terminal pole shoes 16. The skilled person will understand that any other number of magnets 14, pole shoes 15 and terminal pole shoes 16 may be arranged. However, preferable the number of pole shoes 15 and terminal pole shoes 16 exceeds the number of magnets 14 by one.

The terminal pole shoes 16 differ from the pole shoes 15 in their geometry, in particular in their axial length. The terminal pole shoes 16 may be used for determining an axial position of the armature 8. Alternatively or additionally, the material of the terminal pole shoes 16 may differ from the material of the pole shoes 15 in its magnetic permeability to generate a different, e.g. higher, inductance.

The coils 12 and notched metal sheets 13 of the stator 7 are subdivided into a first group 19 and a second group 20. In the illustrated embodiment, the first group 19 extends proximally behind the cartridge 4 along a distance corresponding to the length of the armature 8. The second group 20 is coaxially arranged over at least a substantial part of the length of the cartridge 4 such as approximately 80% of this length. The skilled person will understand that the second group 20 may extend over any other fraction of the length of the cartridge 4 or over its full length. In the illustrated embodiment the first group 19 comprises eight coils 12 and nine metal sheets 13 and the second group comprises 13 coils 12 and 14 metal sheets 13, wherein the first group 19 and the second group 20 share one of the metal sheets 13 where they adjoin each other.

The first group 19 serves for guiding the armature 8 and is arranged for generating an external magnetic field for advancing the armature 8 when the cartridge 4 is full. An air gap 21 between the first group 19 and the armature 8 is particularly small, e. g. less than 1 mm, thus efficiently using the available space and achieving a high degree of efficiency. The magnetic latching forces and thrust forces acting on the armature 8 are significantly determined by the air gap 21 between the notched metal sheets 13 and the pole shoes 15, 16. This allows for a precise adaptation to the requested thrust parameters in the operating area of the first group 19. In an exemplary embodiment, due to this adaptation the minimum latching forces of the armature may be lower than 1N when the coils 12 are turned off, the thrust forces may be higher than 20N when the coils 12 are supplied with a current.

Figure 2:
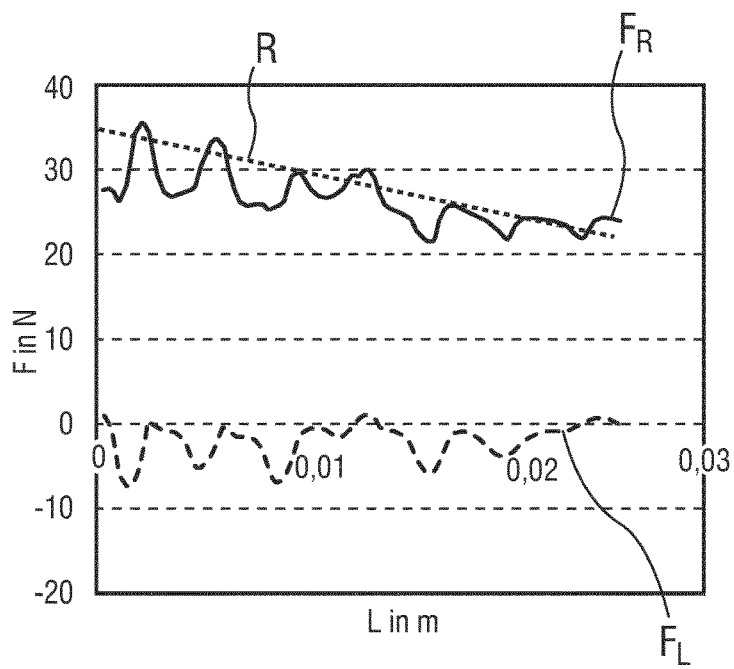
FIG. 2 is a diagram of forces exerted on the armature by the first group of coils depending on an axial position of the armature.
Figure 3:
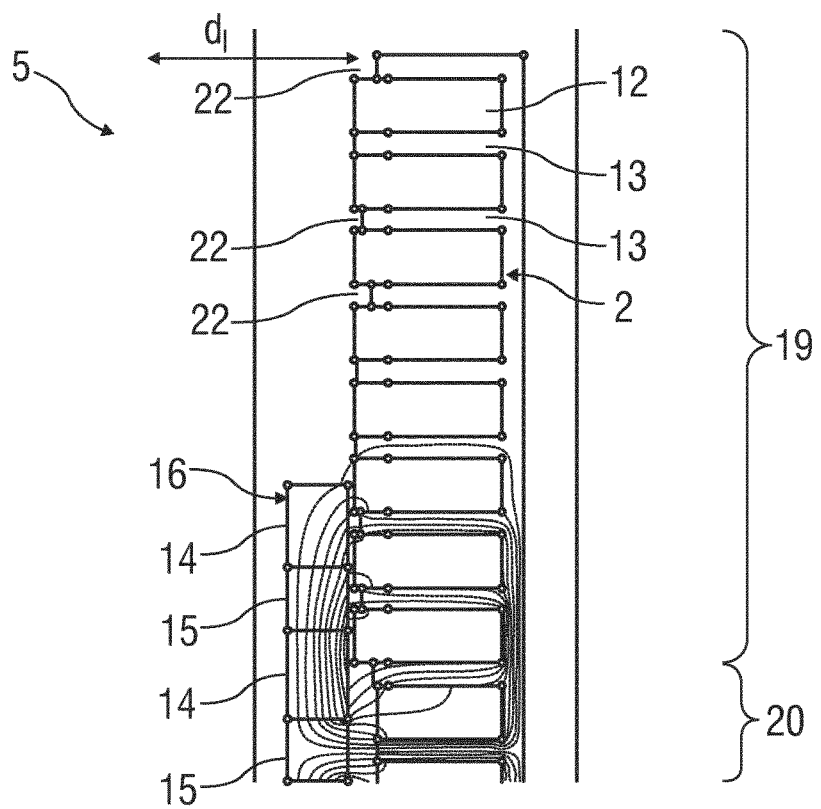
FIG. 3 is a schematic sectional detail view of the drive unit.

FIG. 2 is a diagram of forces F exerted on the armature 8 by the first group 19 of coils 12 depending on an axial position L of the armature 8 relative to the stator 7. FIG. 3 is a schematic sectional detail view of the drive unit 5. An inner diameter $d_I$ of notches created by the notched metal sheets 13 may be separately varied such that the gradient of the thrust forces $F_T$ or the latching forces $F_L$ converges to a given characteristic line. Referring again to FIG. 2, the thrust forces $F_T$ converge to a linearly decaying restriction line R when the coils 12 are supplied with a current. The latching forces $F_L$ (retraction forces) are predominantly negative such that the armature moves to a zero position when the coils 12 are turned off thus providing a safety function.

Figure 4:
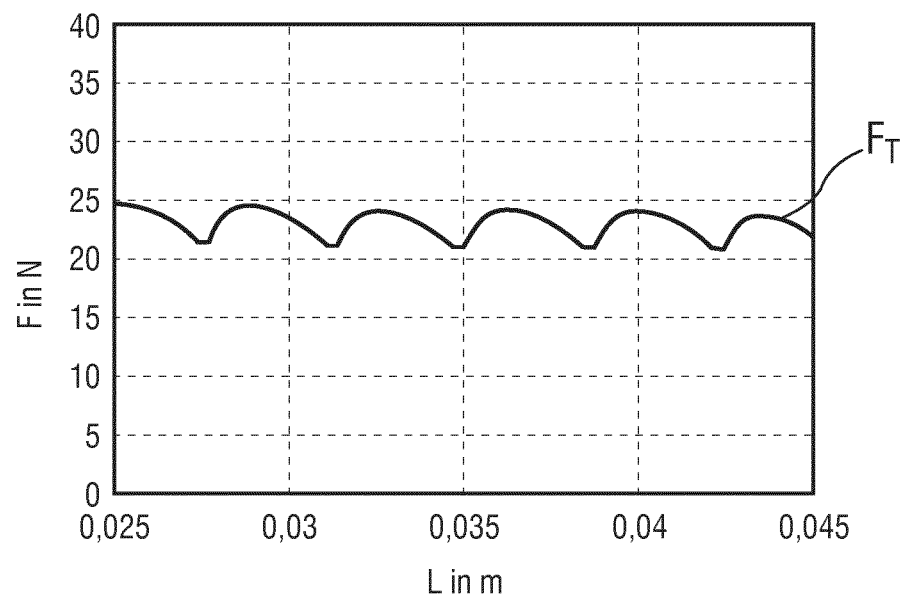
FIG. 4 is a diagram of a thrust force exerted on the armature by the second group of coils depending on the axial position of the armature.

As opposed to the first group 19 the second group 20 of coils 12 has an increased air gap 21 allowing insertion of the cartridge 4. Consequently, the power losses are greater in the second group 20 such that the achievable thrust forces $F_T$ are lower. The smaller air gap 21 of the first group 19 results in higher efficiency and higher forces. FIG. 4 is a diagram of the thrust force $F_T$ exerted on the armature 8 by the second group 20 of coils 12 depending on the axial position of the armature 8 relative to the stator 7. Likewise, the latching forces $F_L$ achievable in the operating area of the second group 20 are lower than in the operating area of the first group 19. In the second group 20 all notches and coils 12 have an identical inner diameter.

In exemplary embodiment, the geometrical parameters of the drug delivery device 1 are selected such that a relation of the thrust force $F_T$ to the latching force $F_L$ is within a range from 15 to 40, in particular 20. For this purpose, the geometrical relations of the drug delivery device 1 may be as follows:

A relation between an external diameter of the stator 7 and an external diameter of the cartridge 4 is within a range from 1.5 to 3, in particular 2.2.

A relation between an external diameter of the armature 8 and the external diameter of the cartridge 4 is within a range from 0.5 to 0.9, in particular 0.8.

A relation between the external diameter of the armature 8 and an internal diameter of the stator 7 is within a range from 0.8 to 0.99, in particular 0.95.

A relation between a length of the stator 7 and a length of the cartridge 4 is within a range from 1 to 1.5, in particular 1.2.

A relation between a length of the armature 8 and the length of the cartridge 4 is within a range from 0.3 to 0.9, in particular 0.61.

A relation between a pole pitch length and the length of the armature 8 is within a range from 0.15 to 0.3, in particular 0.185. The pole pitch length is the sum of the lengths of one of the pole shoes 15 and an adjacent magnet 14.

A relation between the length of one of the poles shoes 15 and a length of one of the terminal pole shoes 16 is within a range from 0.3 to 0.5, in particular 0.43.

A relation between the air gap 21 in the operating range of the first group 19 of coils 12 and the external diameter of the cartridge 4 is within a range from 0.01 to 0.05, in particular 0.02.

In an exemplary embodiment, the thrust force $F_T$ may be 20 N and the latching force $F_L$ may be 1 N.

The axial position of the armature 8 and hence the dosing of the drug can be determined by measuring the inductance of the coils 12 within the stator 7 or by the fluctuation of this inductance.

The inductance L of a long cylindrical coil 12 is determined by the geometry of the coil 12 and is calculated using equation 1 depending on a number N of windings, the magnetic field constant $\mu_0$, the relative permeability $\mu_r$ and the internal cross-sectional area A of the coil 12.

$$L = N^2 \cdot \frac{\mu_0 \mu_r A}{l} \qquad (1)$$

A shorter cylindrical coil 12 exhibits a worse magnetic flux such that the inductance L is estimated by equation 2 additionally taking into account a radius of the winding $r_W$.

$$L = N^2 \cdot \frac{\mu_0 \mu_r A}{l + 2r_W/2, 2} \qquad (2)$$

In order to modify the inductance L different core materials with different relative permeability $\mu_r$ can be used in a coil. Ferromagnetic materials such as iron, which has a relative permeability in the range from 300 to 10000, can be used to increase the inductance L. Because of the linear dependence the inductance can be multiplied.

Figure 5:
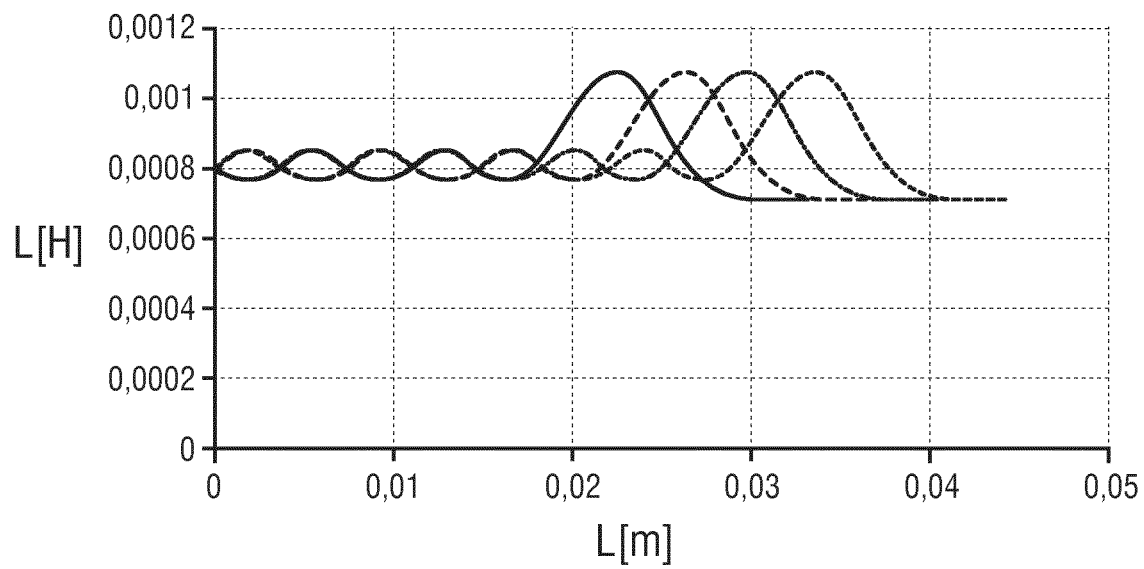
FIG. 5 is a diagram of an inductance of a coil depending on the axial position of the armature.

If a movable core with a varying permeability such as the armature 8 is placed into a coil, the inductance of the coil depends on the axial position of the core. FIG. 5 is a diagram of the inductance L of a number of subsequent coils 12 depending on the axial position of the armature 8 determined using a finite element model. The longer terminal pole shoe 16 at the end of the armature 8 causes an increase of the inductance L as opposed to the shorter pole shoes 15 arranged between the magnets 14. This allows for a more precise determination of the position of the armature 8.

In an exemplary embodiment, the relation of the variation of the inductance L due to the terminal pole shoe 16 to the variation of the inductance L due to the pole shoe 15 is within a range from 2 to 5, in particular 3. In an exemplary embodiment, the variation of the inductance L due to the terminal pole shoe 16 is 150 µH and the variation of the inductance L due to the pole shoe 15 is 50 µH.

In order to apply a thrust force $F_T$ onto the armature 8 for advancing the stopper 6 and dispensing a dose of the drug from the cartridge 4, the coils 12 are supplied with an alternating or pulsed current such that magnetic fields are induced in the coils 12 and interact with the static magnetic fields generated by the magnets 14 of the armature 8.

In order to determine the axial position of the armature 8 within the stator 7 the inductance is determined for the individual coils 12, e.g. by a control unit 18 connected to the individual coils 12. This can be achieved by any conventional method such as applying an alternating voltage to the coil 12, determining an amplitude and phase shift of the resulting current and calculating the inductive reactance and hence the inductance. Likewise, an alternating current may be driven through the coil 12 and an amplitude and phase shift of the resulting voltage can be determined. Likewise, the coil 12 can be connected to a capacitor having a known capacitance to form a resonator whose resonance frequency can be determined by wobbling or by applying a pulse signal and analyzing the answer signal. The inductance can then be calculated from the determined resonance frequency. Likewise, the coil 12 can be connected as part of a bridge network, e. g. a Maxwell bridge for determining the resonance frequency.

As the inductance is much higher in the coils 12 in which one of the terminal pole shoes 16 is located as opposed to the coils 12 where one of the other pole shoes 15 is located, the axial position of the armature 8 and hence the already dispensed dose and/or the dose remaining in the cartridge 4 can be determined.

The inductance of the coils 12 may be determined by the same voltage used to apply the thrust force $F_T$ to the armature 8.

In alternative non-illustrated embodiments the drive unit 5 may be arranged without the geometrical differences between the pole shoes 15 and terminal pole shoes 16 but with the above described different air gaps 21 of the first group 19 and the second group 20.

The term "drug" or "medicament", as used herein, means a pharmaceutical formulation containing at least one pharmaceutically active compound,
wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound,
wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis,
wherein in a further embodiment the pharmaceutically active compound comprises at least one peptide for the treatment and/or prophylaxis of diabetes mellitus or complications associated with diabetes mellitus such as diabetic retinopathy,
wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ie-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 1 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present disclosure, which encompass such modifications and any and all equivalents thereof.

LIST OF REFERENCES 1 drug delivery device
2 case
3 holder
4 cartridge
5 drive unit
6 stopper
7 stator
8 armature
9 tube
12 coil
13 metal sheet
14 magnet
15 pole shoe
16 terminal pole shoe
17 axle
19 first group
20 second group
21 air gap
22 notch
$d_I$ inner diameter
D distal direction
F force
$F_L$ latching force
$F_T$ thrust force
L axial position
P proximal direction
R restriction line

The invention claimed is:

1. A drug delivery device comprising:
a cartridge comprising a body defining a chamber and a stopper slidably arranged within the chamber; and
a drive unit comprising
a stator comprising a plurality of coils consecutively arranged in an axial direction, and
an armature axially movable within the stator and abutting the stopper, the armature comprising a plurality of magnets and a plurality of pole shoes consecutively arranged in the axial direction,
wherein a respective pole shoe of the plurality of pole shoes is arranged between respectively neighboring magnets of the plurality of magnets,
wherein an axial end of the armature comprises a terminal pole shoe, and
wherein a magnetic permeability of one of the plurality of pole shoes differs from a magnetic permeability of the terminal pole shoe.

2. The drug delivery device according to claim 1, wherein:
the stator further comprises a plurality of notched metal sheets in an alternating arrangement with the plurality of coils,
the plurality of coils are divided into a first group and a second group,
the first group extends proximally from the cartridge along a distance corresponding to a length of the armature, and
the second group is coaxially arranged over at least a substantial part of the length of the cartridge, a portion of an air gap along the second group between the plurality of notched metal sheets and the pole shoes being longer relative to a portion of the air gap along the first group between the plurality of notched metal sheets and the pole shoes, the portion of the air gap along the second group being longer than the portion of the air gap along the first group to allow insertion of the cartridge.

3. The drug delivery device according to claim 2, wherein a length of the air gap between the first group and the armature is less than 1 mm.

4. The drug delivery device according to claim 2, wherein an inner diameter of notches defined by the plurality of notched metal sheets varies such that a gradient of thrust forces or latching forces acting on the armature converges to a given characteristic line.

5. The drug delivery device according to claim 4, wherein the thrust forces converge to a linearly decaying restriction line.

6. The drug delivery device according to claim 2, wherein a ratio of a length of an air gap along the first group and between the plurality of notched metal sheets and the plurality of pole shoes to an external diameter of the cartridge is within a range from 0.01:1 to 0.05:1.

7. The drug delivery device according to claim 1, wherein a ratio of an external diameter of the stator to an external diameter of the cartridge is within a range from 1.5:1 to 3:1.

8. The drug delivery device according to claim 1, wherein a ratio of an external diameter of the armature to an internal diameter of the stator is within a range from 0.8:1 to 0.99:1.

9. The drug delivery device according to claim 1, wherein a ratio of a length of one of the poles shoes to a length of the terminal pole shoe is within a range from 0.3:1 to 0.5:1.

10. The drug delivery device according to claim 1, wherein a geometry of the terminal pole shoe differs from geometries of the plurality of pole shoes.

11. The drug delivery device according to claim 1, wherein an axial length of the terminal pole shoe differs from axial lengths of the plurality of pole shoes such that a coil of the plurality of coils in which the terminal pole shoe is located has a different inductance than each of a remainder of the coils in which the plurality of pole shoes are located.

12. The drug delivery device according to claim 1, wherein a control unit is connected to the plurality of coils, the control unit being configured to
determine inductances of the plurality of coils, and
determine an axial position of the armature within the stator from the determined inductances.

13. The drug delivery device according to claim 1, wherein the stator further comprises a plurality of notched metal sheets in an alternating arrangement with the plurality of coils.

14. The drug delivery device according to claim 1, wherein the plurality of magnets are axially magnetized.

15. The drug delivery device according to claim 14, wherein consecutive ones of the plurality of magnets exhibit alternating magnetic polarity.

* * * * *

UNITED STATES PATENT AND TRADEMARK OFFICE
CERTIFICATE OF CORRECTION

| | | |
|---|---|---|
| PATENT NO. | : 10,682,459 B2 | Page 1 of 1 |
| APPLICATION NO. | : 15/538729 | |
| DATED | : June 16, 2020 | |
| INVENTOR(S) | : Christian Nessel et al. | |

It is certified that error appears in the above-identified patent and that said Letters Patent is hereby corrected as shown below:

On the Title Page

Column 1 (Applicant), Line 5 (approx.), delete "Deutschand" and insert -- Deutschland --

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*